United States Patent [19]

Belykh et al.

[11] Patent Number: 5,011,493

[45] Date of Patent: Apr. 30, 1991

[54] MATERIAL FOR CONNECTING MEMBERS FOR INNER SOFT TISSUES AND ORGANS

[76] Inventors: Sergei I. Belykh, 2 Krestovsky pereulok, 4, kv. 66; Vladimir S. Gigauri, Leninsky prospekt, 144, korpus 5, kv. 56; Anatoly B. Davydov, ulitsa Krasny Kazanets, 19, korpus 1, kv. 283; Viktor V. Keshelava, ulitsa Zelenodolskaya, 17, korpus 4, kv. 68; Vyacheslav E. Mlynchik, ulitsa Oktyabrskaya, 38, korpus 1, kv. 43; Rustam I. Utyamyshev, prospekt Mira, 118, kv. 222; Elizaveta V. Firsova, ulitsa Ostrovityanova, 27, korpus 2, kv. 93, all of Moscow, U.S.S.R.

[21] Appl. No.: 105,460

[22] Filed: Oct. 2, 1987

Related U.S. Application Data

[63] Continuation of Ser. No. 769,621, Jul. 1, 1985.

[30] Foreign Application Priority Data

Apr. 14, 1983 [SU] U.S.S.R. .................. 3578808

[51] Int. Cl.$^5$ .......................... A61B 17/08; A61F 2/00
[52] U.S. Cl. ..................... 606/215; 606/214; 606/151; 606/153; 606/154; 600/37
[58] Field of Search .................. 600/37; 606/213, 214, 606/215, 151, 153, 154

[56] References Cited

U.S. PATENT DOCUMENTS

| | | | |
|---|---|---|---|
| 3,144,391 | 8/1964 | Goff | 424/80 |
| 3,527,224 | 9/1970 | Rabinowitz | 606/214 |
| 3,577,516 | 5/1969 | Gould | 424/80 |
| 3,847,155 | 11/1974 | Bernaola | 606/214 |
| 3,914,403 | 10/1975 | Valan | 424/80 |
| 4,310,509 | 1/1982 | Bergland | 424/80 |
| 4,323,557 | 4/1982 | Rosso | 424/80 |
| 4,524,061 | 6/1985 | Cho | 424/81 |

*Primary Examiner*—Alan W. Cannon
*Attorney, Agent, or Firm*—Burgess, Ryan & Wayne

[57] ABSTRACT

A material for connecting members for soft tissues and inner organs which consists of a copolymer of N-vinylpyrrolidone and alkyl esters of acrylic and/or methacrylic acid containing in the alkyl group 2 to 8 carbon atoms at the following proportions of the components, molar percent:

| | |
|---|---|
| N-vinylpyrrolidone | 40–90 |
| alkyl esters of acrylic and/or methacrylic acid | 10–60. |

5 Claims, No Drawings

MATERIAL FOR CONNECTING MEMBERS FOR INNER SOFT TISSUES AND ORGANS

This application is a continuation of application Ser. No. 769,621 filed Jul. 1, 1985.

FIELD OF THE INVENTION

The present invention relates to medicine and, more particularly, to a material for connecting members for soft tissues and inner organs.

BACKGROUND OF THE INVENTION

Known in the art are connecting members from a biological tissue which are adapted for increasing the suture tightness and improving its tenacity to avoid post-operational complications.

Thus, in operations on intestine as sealing connecting members for the above-mentioned purposes epipolic shields are used (cf. A. A. Zaporozhets "Vestnik Khirurgii im. Grekova", (Grekov Surgical Newsletters,) 1964, No. 1, p. 52).

However, a reliable fixation of tissues is not ensured in this case owing to low tenacity characteristics of the epiploic tissue. Furthermore, the use of epiploic shields does not exclude the formation of commissures.

It is also known to employ for the same purposes, in the case of reinforcing an esophageal membrane, a free dermal autotransplantant (cf. T. T. Daurova, A. P. Majsyuk. Experimental Surgery (Eksperimental'naya Khirugiya), 1959, No. 6, p. 37). The use of a dermal autotransplantant ensures a more reliable fixation as compared to epiploic shields, but this necessitates a more complicated preliminary operation with the formation of a new additional trauma. Furthermore, the use of connecting members of a biological tissue is associated with post-operational complications due to disruption (unsoundness) of the suture because of frequent suppurations and the occurrence of extremely undesirable commissural processes is observed.

Known in the art is a material for connecting members for soft tissues and inner organs based on biodegradable synthetic polymers, namely polyvinylformal (cf. T. T. Daurova, A. P. Majsyuk. Eksperimentalnaja Khirurgija, 1959, No. 6, p. 37).

However, in the use of this material a low biodegradation of the material takes place and the period of resorption is longer than the period of regeneration of the soft tissues. Furthermore, the use of such connecting members is accompanied by complications such as purulent pleurisy or mediastinitis resulting in death of 60% of experimental animals. Postoperation complications associated with disrupture (unsoundness) of the suture also take place due to frequent suppurations, accumulation of serous fluid, or with a total rejection. Because of the above-mentioned disadvantages the polyvinyl-formal-based material has found no practical applications in the medical practice.

DISCLOSURE OF THE INVENTION

The present invention is directed to the provision, by an intentional selection of a chemical structure of a polymeric macromolecule by combination of hydrophobic and hydrophilic monomeric structural units therein, of a material for connecting members for soft tissues and inner organs which would be capable of fixing dissected parts of soft tissues and inner organs during the period of the tissue regeneration, as well as ensuring physical and biological tightness of the junction and preventing the formation of commissures with the adjacent tissues and organs.

This object is accomplished by providing a material for connecting members for soft tissues and inner organs based on biodegradable synthetic polymers, according to the present invention which comprises a copolymer of N-vinylpyrrolidone and alkyl esters of acrylic and/or methacrylic acids containing in the alkyl radical 2 to 8 carbon atoms, having an intrinsic viscosity of from 0.3 to 0.8 dl/g at the following proportions of the components, molar, per cent:

| | |
|---|---|
| N-vinylprrolidone | 40–90 |
| alkyl esters of acrylic and/or methacrylic acid | 10–60. |

The material according to the present invention for connecting members for soft tissues and inner organs preferably contains, as the alkyl esters of acrylic and/or methacrylic acids, ethylacrylate, butylmethacrylate or a mixture of ethylacrylate with hexylmethacrylate.

It is preferred to use a material for connecting members which consists of a copolymer of N-vinylpyrrolidone and butylmethacrylate at the following proportions of the components, molar per cent:

| | |
|---|---|
| N-vinylpyrrolidone | 60–75 |
| butylmethacrylate | 25–40. |

The material for connecting members according to the present invention combines in itself the capability of the copolymer to biodegradation necessitating a highly hydrophilic character of the macromolecule for a better interaction with the liquid media of the organism with the necessity of ensuring particular physico-mechanical properties requiring hydrophobicity of the material for retaining soundness characteristics for the period of regeneration.

This is accomplished by introducing, into the copolymer macromolecule, hydrophilic units incorporating nitrogen-containing substituents and hydrophobic units containing alkyl substituents.

BEST MODE FOR CARRYING-OUT THE INVENTION

A copolymer of N-vinylpyrrolidone and alkyl esters of acrylic and/or methacrylic acid is obtained by polymerization in solution using radical-type initiators (peroxides, diazo derivatives, photoradiation and the like). The molar ratio between vinylpyrrolidone and the unsaturated ester is varied from 4:1 to 2:3.

The connecting members for fixation of soft tissues and inner organs which are produced from the material according to the present invention comprise films of various size and configuration having an area of from 20 to 200 cm$^2$ and a thickness of from 30 to 300$\mu$. The films are cast from a 15–50% solution of the copolymer in a mixture of ethanol-butanol (4:1 by volume) using a Teflon or polyethylene substrate. Drying is effected at a step-wise elevation of temperature within the range of from 20° to 40° C. For a better conservation, prior to packing the films are wetted by keeping in the air for 2 hours at the temperature of 20° C. under 100% humidity conditions. Sterilization of samples is effected by the radiation sterilization method at the dose of 2.5 mRad or by keeping in vapours of paraform for 18 hours, followed by residence in a physiological solution for 20 minutes.

Fixation of the connecting members from the material according to the present invention on the injured surface is effected in the following manner.

The connecting members of a size exceeding the geometrical dimensions of the injury are kept for 10-15 minutes in a sterile physiological solution or in Hank's solution. Then a portion of the desired configuration is cut out by scissors according to the size of the injury, dried with a gauze tampon and on one of its faces a layer of a medicinal adhesive is applied. Then the member is applied, with its adhesive side, to the surface of the injured organ or a preformed suture after a preliminary drying thereof with a gauze tampon and then slightly pressed thereto. The sealing of sutures having a complicated shape can be effected by means of several films with an obligatory partial overlapping of the films.

After 60-80 seconds the film becomes soundly glued to the surface. The marginal areas of the film stripping from the surface should be cut off by sterile scissors.

A preliminary evaluation of the functional suitability of connecting members of the material according to the present invention was effected in experiments in vitro using distilled water as a model medium in assessing physico-mechanical characteristics and using a buffer phosphate solution with the pH of 7.4 for assessing biodegradation properties. Since the copolymer molecule contains hydrophilic units, the film swelling and, hence, physico-mechanical properties should depend, to a substantial extent, on the content of nitrogen. An increased content of nitrogen in the copolymer results in a reduced ultimate tensile strength of the samples preliminarily subjected to swelling for one hour. At an increased content of nitrogen above 8% the value of the ultimate tensile strength becomes lower than the minimum allowable value, wherefore the use of copolymers with a higher content of nitrogen becomes impossible.

Taking into account the requirement that the connecting members should not exert a traumatic effect on the adjacent tissues due to a mechanical irritation, as well as the fact that during their application they should be well shaped according to the surface configuration of the injured organ, an essential parameter of the functional suitability of the material according to the present invention is its elasticity which is assessed by the value of a relative elongation at rupture.

As a result of appropriate tests it has been found that the value of a relative elongation at rupture $\Delta l/l$ essentially depends on the content of N-vinylpyrrolidone, namely that it is increasing with a higher content of the latter. However, for all copolymers the value of $\Delta l/l$ exceeds 100%, i.e. the value chosen as the lower limit of elasticity of the material.

The study of dynamic changes of physico-mechanical characteristics in a model medium enabling, to a certain extent, forecasting of reliability of fixation of soft tissues of the organism has shown that with a longer residence time in the model solution the ultimate tensile strength of the film is increased, while the relative elongation at rupture is lowered. This variation of physico-mechanical characteristics is positive, since a higher tenacity ensures, during the entire period of regeneration, the fixation strength of not less than its initial value, while a greater rigidity hinders falling apart of the dissected parts of inner organs under the effect of constant loads.

The material for connecting members according to the present invention has been experimentally tested on animals and in clinics on patients.

In the course of clinical studies the connecting members for soft tissues and inner organs were used for hemostasis, physical and biological sealing of sutures and prevention of commissures in operation on various inner organs and in therapy of different pathological disturbances. The data on the number and character of operations in which the connecting members according to the present invention have been used during extensive clinical experiments are shown in Table 1 hereinbelow.

TABLE 1

Number of operations and possibility of using connecting members from the material of the present invention for inner organs

| Function of the connecting members and kind of the operated organ | Number of operations |
|---|---|
| 1 | 2 |
| Sealing of sutures in stomach resections | 37 |
| Sealing of sutures in operations on esophagus and intestine | 24 |
| Hemostasis and sealing of sutures in operations on liver | 7 |
| Sealing and reinforcement of sutures in operations on lungs | 6 |
| Sealing of anastomoses of a vessel | 1 |
| Hemostasis and sealing of a bladder bed | 8 |
| Sealing of the pancreas tail | 5 |
| Sealing of urogenital organs | 5 |
| Sealing of larynx defects | 4 |
| Sealing of sutures in the mouth cavity after ectomy of salivary glands | 17 |
| Closing of perforations of tympanic membranes | 2 |
| Prophylaxis of commissural processes in osteosynthesis of tubular bones | |
| Total: | 128 operations |

The tests were performed with the use of connecting members having three different sizes as shown in the following Table 2.

TABLE 2

| | Characteristics of connecting members | | |
|---|---|---|---|
| Types of connecting members | Length, mm | Width, mm | Thickness, $\mu$ |
| Version 1 | 100 | 75 | 100 |
| Version 2 | 75 | 50 | 100 |
| Version 3 | 50 | 37 | 100 |

We have studied most comprehensively the application of the material for connecting members according to the present invention to sealing of sutures in the treatment of stomach and gastro-intestinal track diseases.

Good results have been obtained in the treatment of complicated forms of peptic ulcer of different localizations. The sealing of sutures by means of the material according to the present invention was performed in two extended stomach resections (⅔) with anastomisis according to Bilrot-1 two stomach resections (⅔) with anastomosis according to Bilrot-2, two antrectomies in combination with vagotomy of two sparing resections (¼ and ⅓) with anastomosis according to Bilrot-1 of two reconstructive (reduodenization) operations and in one case—in the creation of an artificial esophagus from the right half of the large intestine. All the patients were sent home fully recovered. Post-operation complications were observed only in one case. An infiltrate was formed after stomach resection for the reason of the upper third ulcer; after an appropriate treatment the infiltrate was fully resorbed.

The use of the material for connecting members according to the present invention has proven successful also in the treatment of oncological diseases of the distal part of stomach. The material according to the present invention in combination with medicinal adhesive was used during tests for physical and biological sealing of sutures in 18 stomach resections and 9 gastroenterostomies with intestinal anastomosis. The sealing was effected by way of a gradual adhesive application of narrow strips of the material according to the present invention till a full closure of the entire suture line. The films were glued with a certain overlapping. This technique has considerably facilitated a full closure of the anastomosis line and ensured a high sealing tightness. It should be noted that the duration of an operation with the use of the material according to the present invention was only 3–4 minutes longer than that of an operation performed according to a generally accepted control procedure.

A comparative study of the reasons of post-operation peritonitises after stomach resection have shown that upon reinforcement of the anastomosis zones by connecting members from the material according to the present invention no disruption of the sutures is observed. Upon reinforcement of intestinal anastomoses in gastroenterostomies by means of the connecting members according to the present invention the complications of the above-mentioned type were observed only in 1 case out of 9 which is substantially lower than in the control group.

During the same period 32 patients were operated for oncological diseases, on 15 persons the material according to the present invention was used. Only in 3 patients out of 15 post-operation complications were observed for the reason of suture suppuration, while in the control group the number of complications was 6 out of 17.

By means of only connecting members from the material according to the present invention it was possible to seal the wound surface of the parenchyma remained after resection of a portion of a lung with the area of 8×12 cm without using suturing instruments. However, such effect was not reached in all of the cases. Application of an adhesive onto a large-size surface by means of a needle with which an ampule with the adhesive is provided is rather difficult and time-consuming. This causes an untimely polymerization of the adhesive in some areas. In 3 cases out of 6 by the end of operation when the lung blowing was effected; the film was stripped off the lung wound. In three remaining cases the film was stripped only at the edges and ensured fixation of the parenchyma. In these three patients the post-operation period proceeded usually with an insignificant evolution of air via drains. No post-operation suppuration was observed. These results make it possible to advise the use of the material according to the present invention in operations on lung parenchyma. However, to increase the sealing reliability, it is necessary to use a procedure employed for sealing of intestinal anastomoses, i.e. the formation of a solid seam by glueing narrower films fixed with a certain overlapping.

Upon the ectomy of the gallbladder the film is reliably fixed on the liver surface. No bleeding is observed on the edges. The post-operation period in all 8 cases proceeded without complications.

A reliable hemostasis with the use of the material according to the present invention was obtained in 3 cases out of 4, in 1 case the film glued to the diaphragm was torn away together with the gauze tampon that fixed it. In three cases the post-operation progress was smooth, no complications were observed.

For biological sealing of sutures and increasing their soundness, the material according to the present invention was used in the formation of sutures in the mouth cavity after the ectomy of tumors of salivary glands for the reason of the sialolithic disease and their chronic inflammation. The film was placed inside soft tissues with a subsequent suturing. In all of 17 cases the post-operation progress was smooth, the wounds were healed by primary tension.

To ensure an anticommissural effect, the material according to the present invention was used in operations for fractures of tubular bones (thighbone, crus). The films were applied without using medicinal adhesive under fascia and along the sutures until a full closure thereof. In the case of large areas a point fixation of the film by means of an adhesive was effected. The control of the formation of commissures was effected by palpation within the period of from 1 to 4 months and according to the patients'testimony. In all cases there was noticed the absence of the commissure formation. In three cases the absence of commissures was noted visually. In one patient upon a repeated operation after 6 months for the removal of a metallic plate there was noticed the absence of commissures at a full fragmentation of the film with the detection of individual microflagments. In two other patients subjected to the same repeated operations after 8 and 8.5 months it was impossible to find traces of the film; no formation of commissures was also noticed.

In all cases no deviations were noticed in analyses of blood, urine, as well as no presence of any local tissue response to the material according to this invention.

The connecting members of the material according to the present invention are convenient in use, their configuration can be readily adapted to any required shape by means of conventional surgical scissors, they can be easily shaped over the surface of the injured organ.

The application of the connecting members from the material of the present invention ensures a reliable juxtaposition of the dissected portions of soft tissues; it precludes the occurrence of commissural processes; precludes post-operation haemorrages; causes no reaction of the organism to the connecting member as to a foreign body due to complete resorption of the connecting member.

For a better understanding of the present invention illustrative examples are given hereinbelow of the material according to the invention for connecting members for soft tissues and inner organs.

EXAMPLE 1

Copolymer of N-vinylpyrrolidone and ethylacrylate containing 50 mol. % of vinylpyrrolidone units.

This copolymer is produced by copolymerization in toluene at the temperature of 80° C. in the presence of 0.5% molar porophore 4A4C/4,4-aza-bis-(4-cyanpentanoic acid)/of 7.8 g of N-vinylpyrrolidone and 3 g of ethylacrylate. The yield of said copolymer is 9.7 g $[\eta]==0.43$ dl/g. Films with the thickness of $250\mu$ are obtained by casting from a 26% solution of the copolymer in chloroform. Tensile strength, $\sigma_t = 14$ kg/cm$^2$, relative elongation after 30 min keeping in physiological solution $\epsilon_{30} = 90\%$, the time of resorption in the organism is 95–100 days.

EXAMPLE 2

Copolymer of N-vinylpyrrolidone and octylacrylate containing 43 mol. % of vinylpyrrolidone units.

This copolymer is produced by copolymerization of 6.6 g of N-vinylpyrrolidone and 7.3 g of octylacrylate in the presence of porophore 4A4C at the temperature of 85° C. in toluene. The desired product yield is 10.6 g $[\eta]==0.34$ dl/g. Films of the thickness of 170$\mu$ are obtained by casting from a 32% solution of the copolymer in chloroform; $\sigma_t=16.7$ kg/cm$^2$; $\epsilon_{30}=210\%$, time of resorption in the organism—240-280 days.

EXAMPLE 3

Copolymer of N-vinylpyrrolidone and butylmethacrylate containing 55.2 mol. % of vinylpyrrolidone units.

This copolymer is produced by copolymerization of 7.77 g of N-vinylpyrrolidone and 4.26 g of butylmethacrylate in the presence of porophore 4A4C at the temperature of 75° C. in benzene. The yield of the desired product is 9.8 g $[\eta]=0.78$ dl/g.

Films with the thickness of 200$\mu$ are obtained by casting from a 24% solution of the product in an alcohol. $\sigma_t=18$ kg/cm$^2$, $\epsilon_{30}=34\%$, the time of resorption in the organism is 130-150 days.

EXAMPLE 4

Copolymer of N-vinylpyrrolidone and butylmethacrylate containing 79.8 mol. % of vinylpyrrolidone units.

This copolymer is produced by copolymerization of 8.8 g of N-vinylpyrrolidone and 2.8 g of butylmethacrylate in the presence of porophore 4A4C at the temperature of 85° C. in benzene. The desired product yield is 10.2 g, $[\eta]=0.62$ dl/g. In a manner similar to that of Example 3, films with a thickness of 40-60$\mu$ are produced; $\sigma_t=6.4$ kg/cm$^2$, $\epsilon_{30}=880\%$, the time of resorption in the organism is 35-40 days.

EXAMPLE 5

Copolymer of N-vinylpyrrolidone and butylmethacrylate containing 41.1 mol. % of vinylpyrrolidone units.

This copolymer is produced by copolymerization, in a manner similar to that described in Example 3, of 4.4 g of N-vinyl pyrrolidone and 8.25 g of butylmethacrylate. The yield of the desired product is 11.3 g, $[\eta]=0.73$ dl/g.

As described in Example 3 hereinbefore, films with the thickness of 240$\mu$ are obtained; $\sigma_t=18.8$ kg/cm$^2$, $\epsilon_{30}=110\%$, the time of resorption in the organism is 315-330 days.

EXAMPLE 6

Copolymer of N-vinylpyrrolidone, ethylacrylate and hexylacrylate containing 57.3 mol. % of vinylpyrrolidone units.

This copolymer is produced in a manner similar to that described in Example 3 from 7.77 g of N-vinylpyrrolidone, 1.0 g of ethylacrylate and 3.12 g of hexylacrylate. The copolymer yield is 10.6 g, $[\eta]=0.41$ dl/g.

Sheets with the thickness of 1.5 mm are produced by compression-moulding at the temperature of 140° C. under the pressure of 80 kg/cm$^2$; $\sigma_t=13.3$ kg/cm$^2$, $\epsilon_{30}==105\%$, the time of resorption in the organism is 164-170 days.

EXAMPLE 7

Copolymer of N-vinylpyrrolidone and pentylmethacrylate containing 89.6 mol. % of vinylpyrrolidone.

This copolymer is produced by copolymerization of 10.5 g of N-vinylpyrrolidone and 0.78 g of pentylmethacrylate in the presence of 0.6% by weight of porophore 4A4C at the temperature of 84° C. in xylene. The copolymer yield is 10.2 g, $[\eta]=0.32$ dl/g. Films with a thickness of 80-90$\mu$ are produced by casting from a 37% solution in a mixture of ethanol and butanol (volume ratio of 9:1); $\sigma_t=3.2$ kg/cm$^2$, $\epsilon_{30}=910\%$, the time of resorption in the organism is 15-25 days.

INDUSTRIAL APPLICABILITY

The material for connecting members for soft tissues and inner organs according to the present invention is useful in medicine for hemistasis, physical and biological sealing of sutures and prevention of the formation of commissures in operations on various inner organs and in the treatment of various pathological disturbances.

We claim:

1. A method wherein members of soft tissue and inner organs located within a subject have been partially or completely separated and are thereafter reconnected, which comprises reconnecting the separated portions thereof with a biodegradable synthetic polymer, consisting essentially of a copolymer of N-vinylpyrrolidone and alkyl esters of acrylic and/or methacrylic acids containing 2 to 8 carbon atoms in the alkyl group, and having an intrinsic viscosity of from 0.3 to 0.8 dl/g in the following proportions of the components, in molar per cent:

| | |
|---|---|
| N-vinylpyrrolidone | 40-90 |
| alkyl esters of acrylic or methacrylic acids | 10-60. |

2. The method of claim 1 wherein said biodegradable synthetic polymer is in the form of a film.

3. The method of claim 1 wherein said biodegradable synthetic polymer is in the form of a strip.

4. The method of claim 1 wherein said alkyl esters of acrylic and/or methacrylic acids are selected from the group consisting of ethylacrylate, butylmethacrylate, and a mixture of ethylacrylate with hexylmethacrylate.

5. The method of claim 1 wherein said biodegradable synthetic polymer consists essentially of a copolymer of N-vinylpyrrolidone and butylmethacrylate in the following proportions of the components in molar per cent:

| | |
|---|---|
| N-vinylpyrrolidone | 60-75 |
| butylmethacrylate | 25-40. |

* * * * *